United States Patent [19]

Sjostrom et al.

[11] Patent Number: 4,705,038
[45] Date of Patent: Nov. 10, 1987

[54] SURGICAL SYSTEM FOR POWERED INSTRUMENTS

[75] Inventors: Douglas D. Sjostrom, Wakefield; Edvin Zemgals, Pinehurst, both of Mass.

[73] Assignee: Dyonics, Inc., Andover, Mass.

[21] Appl. No.: 693,779

[22] Filed: Jan. 23, 1985

[51] Int. Cl.$^4$ ............................................. A61F 17/23
[52] U.S. Cl. ............................... 128/305; 128/303 R; 604/22
[58] Field of Search ..................... 128/305, 305.1, 310, 128/303 R; 604/22

[56] References Cited

U.S. PATENT DOCUMENTS

| | | | |
|---|---|---|---|
| 3,835,858 | 9/1974 | Hagen | 128/305 |
| 3,990,452 | 11/1976 | Murry et al. | 128/305 |
| 4,289,131 | 9/1981 | Mueller | 128/303 R |
| 4,496,342 | 1/1985 | Banko | 604/22 |

OTHER PUBLICATIONS

"Arthroscopic Surgical System", *Dyonics, Inc.*, (dated 2/1/83).
"Arthroplasty System", *Dyonics, Inc.*, (dated 12/15/83).
"Intra-Articular Surgical System II", *Dyonics, Inc.*, (dated 12/15/83).
"Synovectomy System", *Dyonics, Inc.*, (dated 2/1/84).

Primary Examiner—Richard J. Apley
Assistant Examiner—H. Macey

[57] ABSTRACT

A single-motor surgical system for operating a set of different surgical devices having different operational limits, consisting of a handpiece containing the motor and adapted to alternately receive a proximal portion of each of the surgical devices, each device having an indicator on its proximal portion that denotes its operational limit, the handpiece including an automatic sensor for sensing the indicator, and controls responsive to the sensor to automatically establish the operational limit of the motor in accordance with the respective surgical device received by the handpiece. In preferred embodiments, the system includes an arthroscopic handpiece as above and has a plurality of surgical devices adapted to receive different removable rotary tips that have different operational limits of rotation, each of the plurality of devices having a vacuum passage connectible at one end to a vacuum passage of the respective rotary tip and adjacent the other end, to a vacuum passage associated with the handpiece, whereby tissue severed by the rotary tip can be removed from the surgical site, the surgical device indicating to the sensor the rotational limits of the tips which the devices are adapted to receive.

10 Claims, 15 Drawing Figures

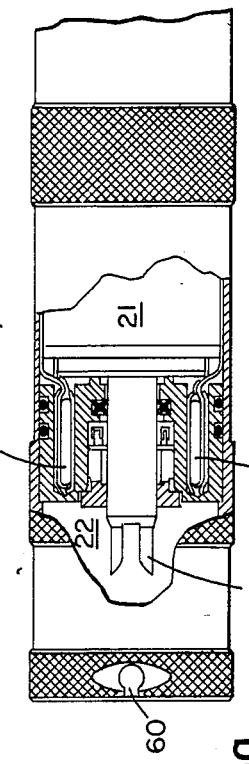
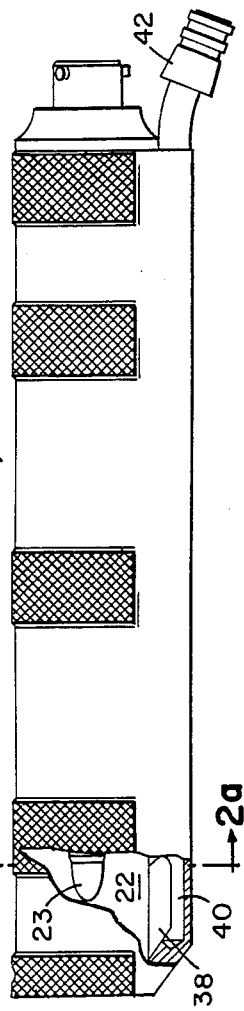
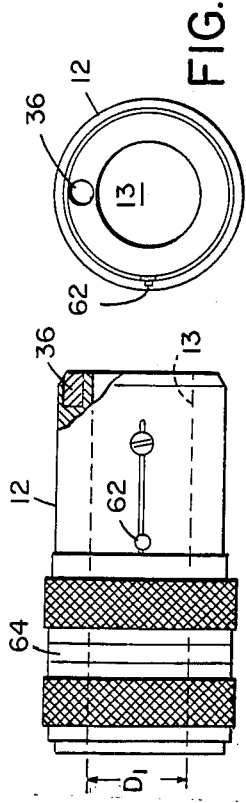
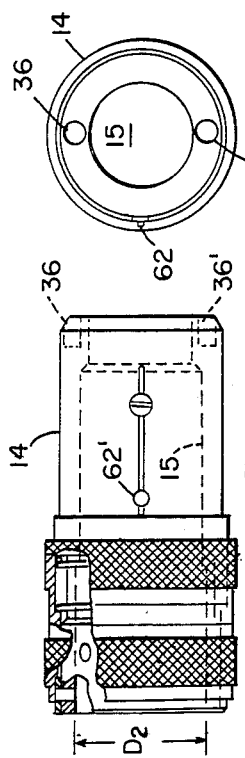
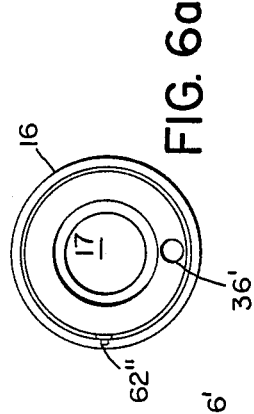
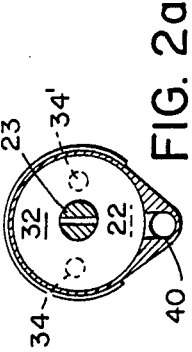
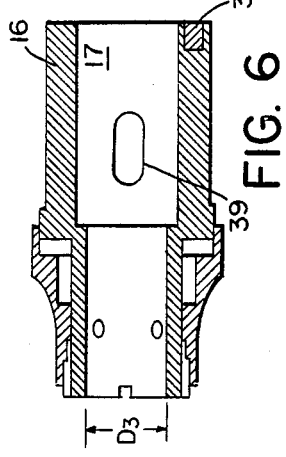

4,705,038

SURGICAL SYSTEM FOR POWERED INSTRUMENTS

BACKGROUND OF THE INVENTION

This invention relates to systems for operating powered surgical instruments.

Operating tips for cutting and abrading tissue come in widely different sizes and configurations, each designed for performance of a particular surgical procedure. The optimum operational limits of the different surgical devices are different, for instance as to the speed and torque at which they can safely operate.

If a surgical procedure on a patient requires use of surgical devices of differing characteristics, the surgeon must either have separate motorized units for each device, or a central unit must be adjusted with each device change, a time-consuming operation, and one that entails some risk of error, with possible damage to the instrument or injury to the patient.

Objectives of this invention are to provide a surgical system suitable for use with surgical devices having different operational limits, which enables greater safety, speed and convenience with a single drive unit.

SUMMARY OF THE INVENTION

According to the invention, a single-motor surgical system adapted to operate a set of different surgical devices having different operational limits comprises: a handpiece containing the motor and adapted to alternately receive a proximal portion of each of the surgical devices, each of the surgical devices having an indicator on its proximal portion that denotes its operational limit, the handpiece including automatic sensor means for sensing the indicator; and means responsive to the sensor to automatically establish the operational limit of the motor in accordance with the respective surgical device received by the handpiece.

In preferred embodiments, the system includes an arthroscopic handpiece constructed as above and a plurality of surgical devices adapted to recieve different removable rotary tips that have different operational limits of rotation, each of the plurality of the devices having a vacuum passage connectible at one end to a vacuum passage of the respective rotary tip and, adjacent the other end, to a vacuum passage associated with the handpiece, whereby tissue severed by the rotary tip can be removed from the surgical site, the indicators of the surgical devices indicating to the sensor means the rotational limits of the tips which the devices are adapted to receive, preferably a vacuum passage is defined through the handpiece from adjacent the surgical device to adjacent the proximal end of the handpiece, and the handpiece includes means for connecting the vacuum passage to an external source of suction, whereby tissue severed by the rotary tip can be removed from the surgical site through the handpiece; the sensor is adapted to limit the torque applied by the motor and to limit the range of speed of the motor; the motor is electrical and has an associated power source, and the sensor means is responsive to the indicator of a given surgical device to establish a limit on the electrical power delivered by the power source, preferably the sensor means is responsive to limit the voltage applied to the motor and the motor is adapted to maintain its speed in accordance with the voltage applied, and the sensor means is responsive to limit the electrical current applied to the motor to limit the torque delivered by the motor; the indicator for each of the set of surgical devices comprises a magnet means adapted to produce a magnetic field different from that of other surgical devices of the set, the sensor means in the handpiece being responsive to the magnetic field to switch the motor to the respective operational limit; and the surgical devices include magnets in their proximal portions and the handpiece includes a set of switches actuatable by the presence of the magnets.

Other features and advantages of the invention will be understood from the following description of the presently preferred embodiment, and from the claims.

PREFERRED EMBODIMENT

We briefly describe the drawings.

DRAWINGS

FIG. 2 is a plan view, partially in section, of the motorized handpiece of the system of the invention, while FIG. 2a is an end section view of the handpiece at line 2a—2a of FIG. 2;

FIG. 3 is a side view, partially in section, of the distal portion of the motorized handpiece of the system;

FIGS. 4 and 4a are side and end views, respectively, of one surgical device adapted for use in the system of the invention;

FIG. 5 is a side view, partially in section, and FIG. 5a is an end view of another surgical device of the invention;

FIG. 6 is a side section view and FIG. 6a is an end view of still another surgical device of the invention.

Figure 1:
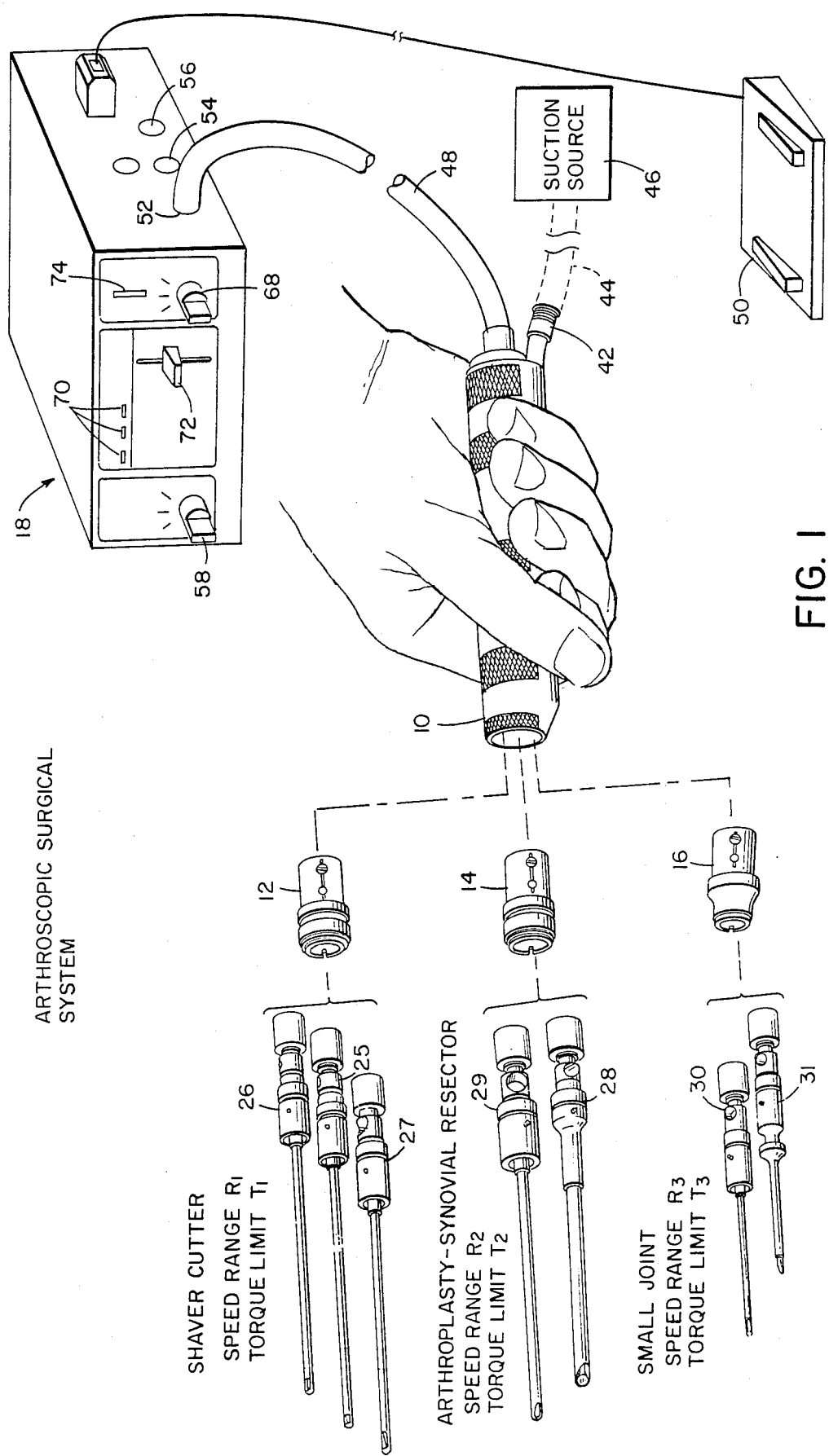
FIG. 1 is a perspective of the system according to the invention.

Referring to FIG. 1, the arthroscopic surgical system of the invention consists of handpiece 10, surgical devices 12, 14, 16, each intended for use within specific preselected operational limits, controller/power unit 18 and foot control 20. Also included are removable rotary tips selectively adapted for use with the surgical devices, as discussed more fully below.

Handpiece 10 includes motor 21, and has a distal recess 22 into which drive shaft 23 extends. The recess is sized and configured to securely receive a proximal portion of the associated surgical devices.

Three such surgical devices are shown. The Shaver/Cutter device 12 has an axial bore 13 of diameter $D_1$, sized and adapted to receive rotary tips having a corresponding outer diameter for operation at rotational speeds in range $R_1$, e.g. from about 100 rpm up to about 3 revolutions per second or 200 rpm, at maximum torque of $T_1$, e.g. 28 inch ounces. Rotary tips useful with this surgical device include the Shaver, Cutter and Trimmer Blade Assemblies, manufactured by Dyonics, Inc. of Andover, Mass. These are indicated by reference numerals 25, 26, 27 in FIG. 1.

Arthroplasty/Synovial Resector device 14 has a larger axial bore 15 of diameter $D_2$, sized and adapted to receive rotary tips of corresponding outer diameter for operation at higher rotational speeds in range $R_2$, e.g. 400 to 1400 rpm, and at maximum torque of $T_2$, e.g. about 28 inch ounces. Rotary tips useful with this surgical device include the Abrader and Full Radius Synovectomy Blade Assemblies, also manufactured by Dyonics, Inc., and are indicated by reference numerals 28 and 29 in FIG. 1.

Small Joint device 16 has an axial bore 17 of diameter $D_3$, sized and adapted to receive rotary tips of configuration similar to those mentioned above, but of smaller size for use within joints offering limited working volume, e.g., the ankle, elbow and wrist joints. Examples of suitable rotary tips are indicated by reference numerals 30 and 31. Device 16 is suited for operation of rotary tips in rotational speed range $R_3$, e.g. about 300 to 1500 rpm, at maximum torque $T_3$, e.g. about 14 inch ounces.

Each rotary tip defines a vacuum passage extending from the distal end of the tip, adjacent the cutting edges, through the rotary tip, to discharge into a vacuum passage defined by the associated surgical device, which serves as a drain case. The vacuum passage of the drain case in turn is connected via outlet 39 in its side wall to an aligned port 38 in the side wall defining the recess into drain tube 40 provided within the handpiece. Adjacent the proximal end of the handpiece the drain tube terminates in connector 42 adapted for attachment to a suction hose 44, e.g. from a wall suction outlet 46, for removal of tissue and fluid from the surgical site. By conducting the fluid through the handpiece to the proximal end, where the connecting hose, as it exits, is substantially parallel to the power cord 48, interference by the suction hose with manipulation of the handpiece by the surgeon is minimized.

Within the handpiece, closely adjacent surface 32 defining the surgical-device-receiving recess, are sensors consisting of end operated mini-reed switches 34, 34'. In the proximal end surface of each of the surgical devices, at selected locations opposite the positions of the sensors when the device is assembled with the handpiece, are magnets 36, 36' adapted to actuate the reed switches. The magnetc indicators in the surgical devices are arranged in predetermined respective patterns, whereby the acuation of the switches opposite the magnet positions identifies to the rest of the system, the device that is to be used. The controller/power unit then automatically establishes a limit on the power to be provided to the handpiece to limit the speed range and the torque to within the preselected limits for optimum performance of the rotary tip being used. This reduces the chance of damage to the surgical device or tip, and reduces the risk of injury to the patient.

The motor compartment of handpiece 10 is sealed, with the reed switches disposed wtihin the compartment, to permit the handpiece to be sterilized by autoclaving. The surgical devices and rotary tips can also be autoclaved.

Referring to FIG. 1, to operate the arthoscopic surgical system of the invention, connect footswitch 50 to the labeled receptacle on the side of the controller/power unit 18. Plug the cord 48 from the motorized handpiece 10 into the proper receptacle 52 on the side of the unit. (In the unit shown, provision is made for operation of motor drive units for the Dyonics, Inc. Intra-Articular Surgical System and the Arthroplasty System by connecting them to receptacles 54, 56 of the power unit. The receptacles are designed so that each motor drive unit will function only if its plug is inserted into the correct receptacle.)

Turn the selector switch 58 at the left of the controller/power unit front panel to its center position, labeled "UNIVERSAL DRIVE". (If another motor drive unit is to be used, turn the selector switch to the appropriate position. Power is supplied only at the selected receptacle.)

Select the desired surgical device, e.g. Shaver/Cutter device 12, bring the handpiece 10 and device 12 together, orienting the handpiece so its key slot 60 can be seen. Orient the device 12 so its key 62 can be seen. Slide the device into the handpiece so that the key enters the slots. Push in until a click is heard. (When it is desired to remove a surgical device, press down on the key and simultaneously draw the device from the handpiece. If suction is being applied, the operator will perceive a slight force holding the components together.)

Each surgical device has a spring-loaded ring 64 at its distal end. This is the release ring that permits rotary tip insertion and removal. (The reference numerals given refer to device 12. Common structural features present in devices 14 and 16 are indicated with the same reference numerals, marked prime and double prime, respectively.)

To attach a rotary tip, slide the release ring on the device toward the handpiece. This will reveal the key slot 66" on the distal rim of device recess (device 16, FIG. 6). Select a rotary tip from the same family as the selected device. (The proximal portions of the rotary tips are selectively sized to fit properly in the bore of only the surgical device with which they are intended to be used.) Orient the handpiece and device so that the key slot 66" on the device and the corresponding key on the tip can both be seen. Insert the tip into the device so that the key goes into the slot. Let the release ring slide back to its original position. (To remove a tip, slide the release ring toward the handpiece, and simultaneously draw the tip out of the device. If suction is being applied, the operator will perceive a slight force holding the components together.)

Before beginning operation, the functions of the system should be tested.

Turn the power unit function selector switch 68 at the lower light of the panel to the ON position.

Turn the motor selector switch 58 at the lower left of the panel to the position corresponding to the handpiece. When the handpiece of the invention is used, one of LEDs 70 at the top of the panel will automatically identify the device being used. If no device is attached to the handpiece, no LED will light and the motor will not run.

Use the speed control 72 at the center of the panel to control the speed of the rotating tip within the range allowed.

Depress the footswitch and check that the blade in the tip goes in both the forward and reverse directions.

Check the charge remaining in the battery by noting which LED is lighted in the bargraph 74 at the top right of the panel. If one of the bottom three LEDs is lighted, the unit should be recharged as soon as possible. The function selector switch 68 must be in the ON (left) position for this reading; turn it to the OFF (center) position when not using or charging the power unit. During operation, it is normal for the LED bargraph reading to change when the footswitch is depressed.

Push the suction tube 44 firmly on the drain connector 42 of handpiece drain tube 40.

Figure 7:
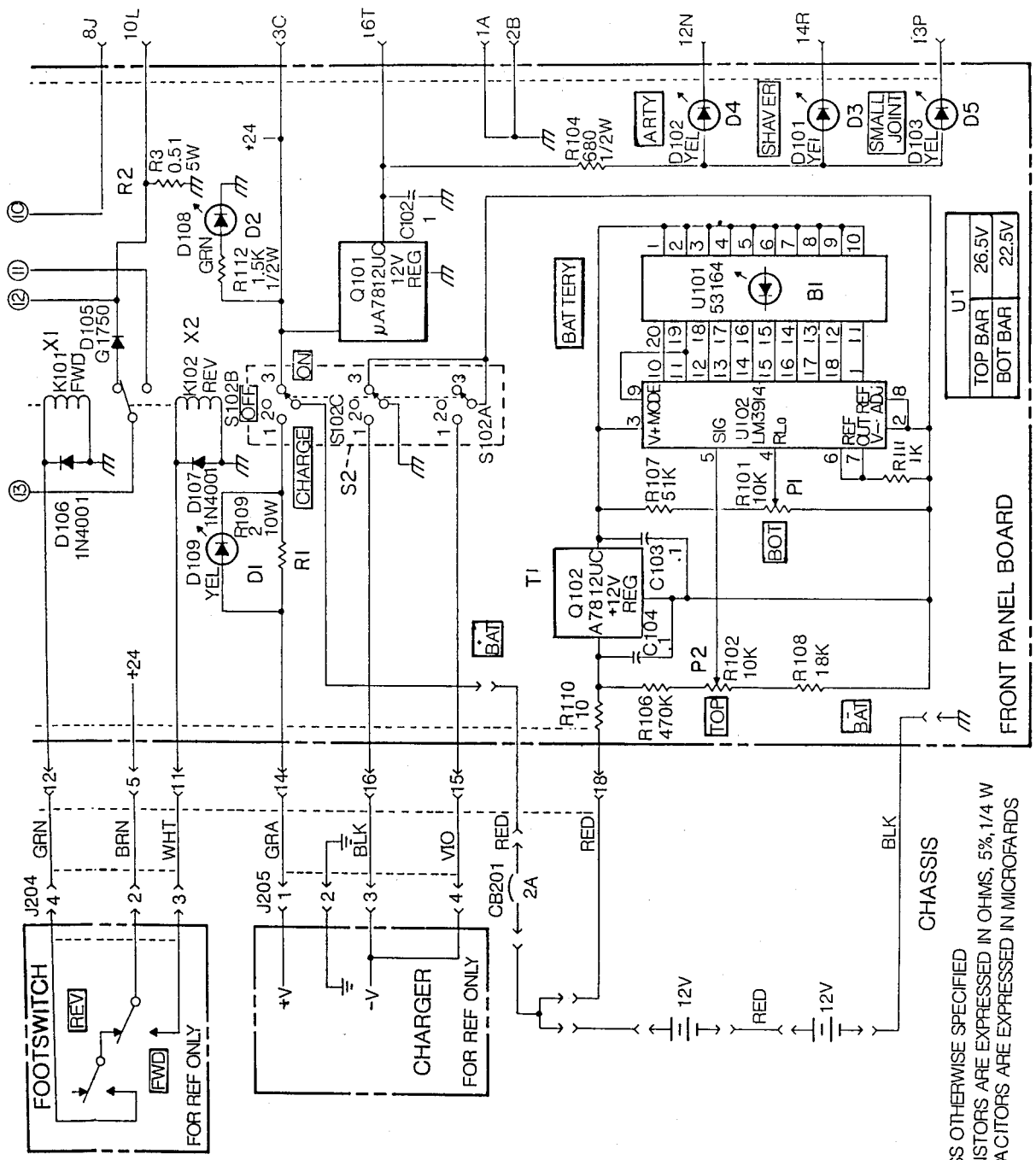
FIGS. 7, 7a, 7b, 7c and 7d are schemmatic diagrams of the circuitry of the system according to the invention.
Figure 7A:
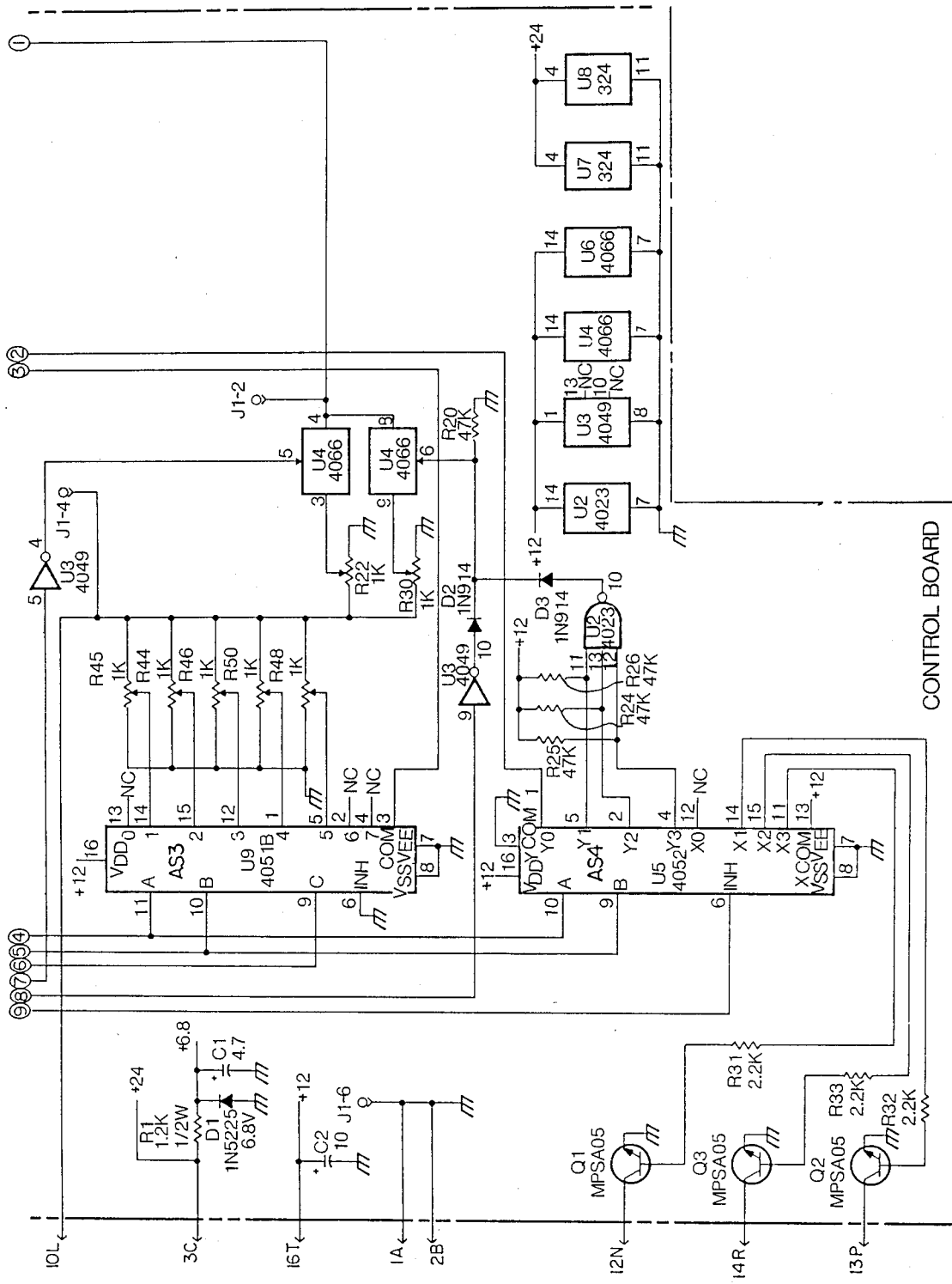
Figure 7B:
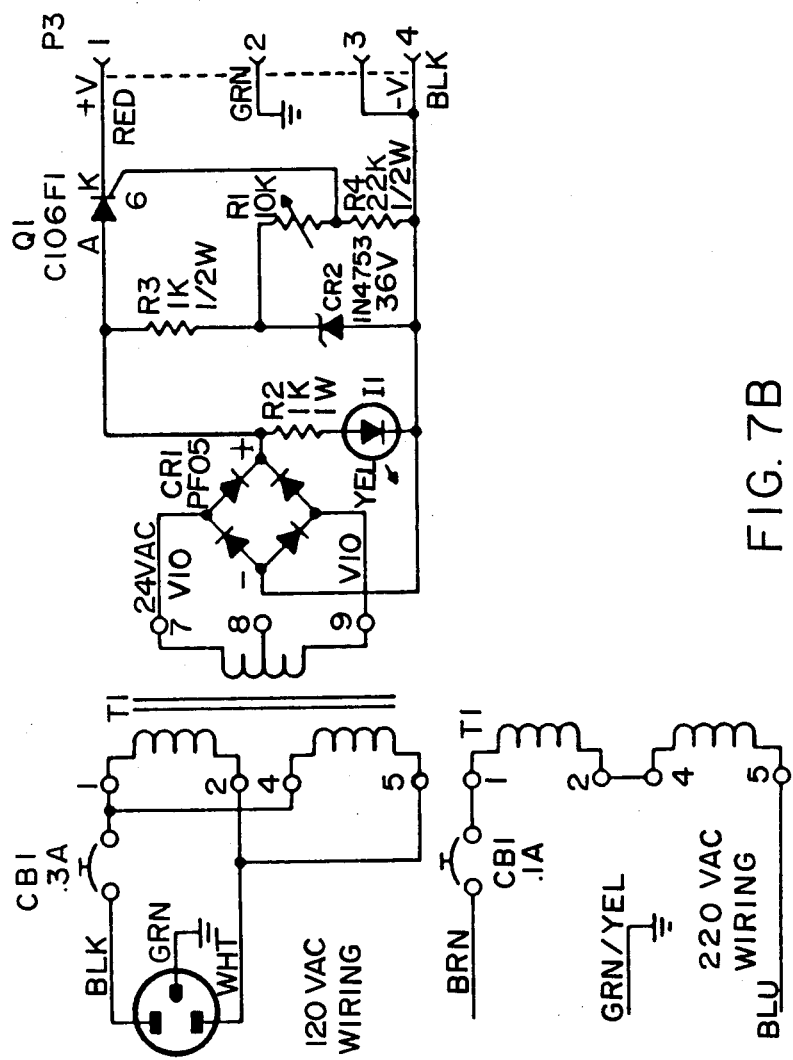
Figure 7C:
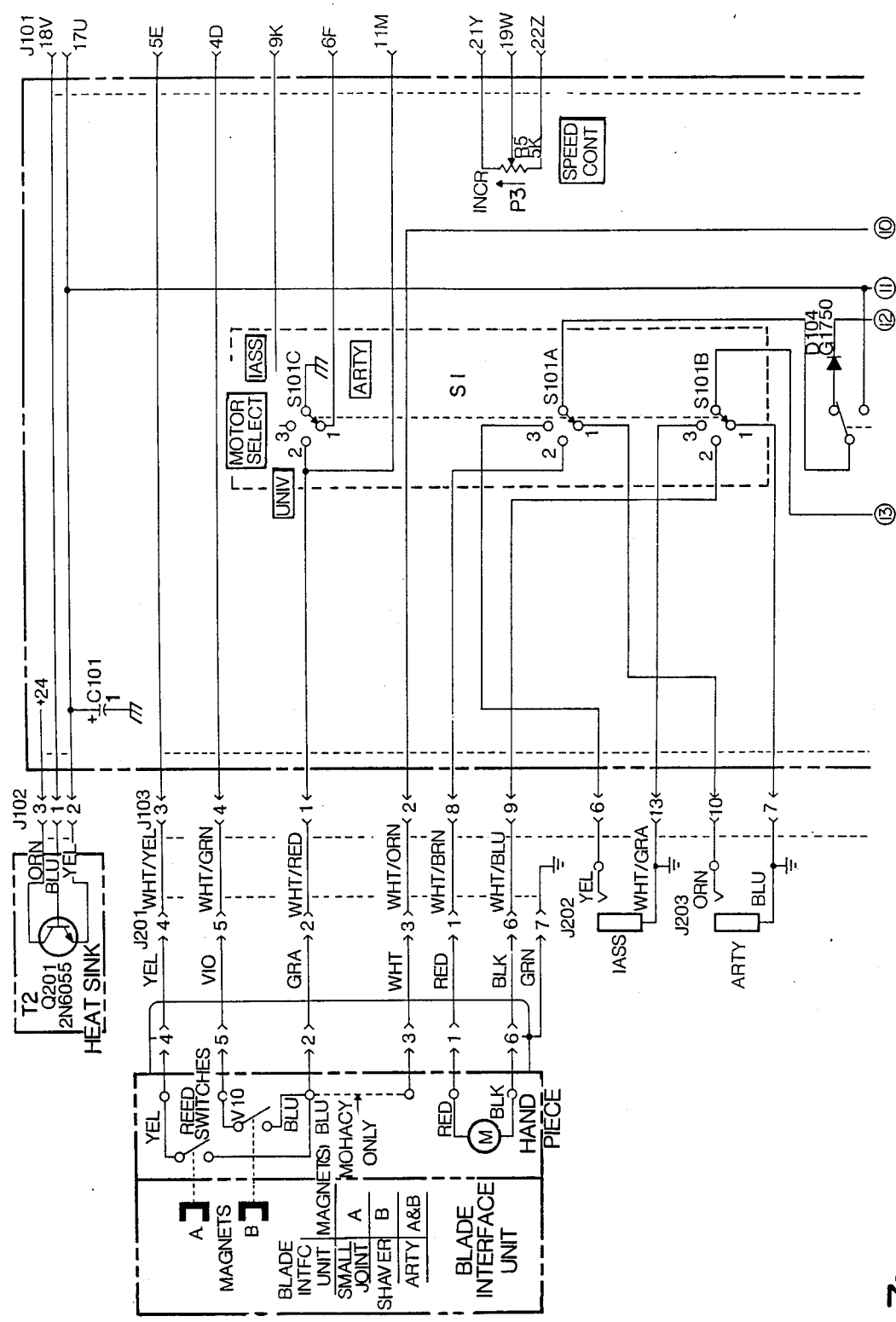
Figure 7D:
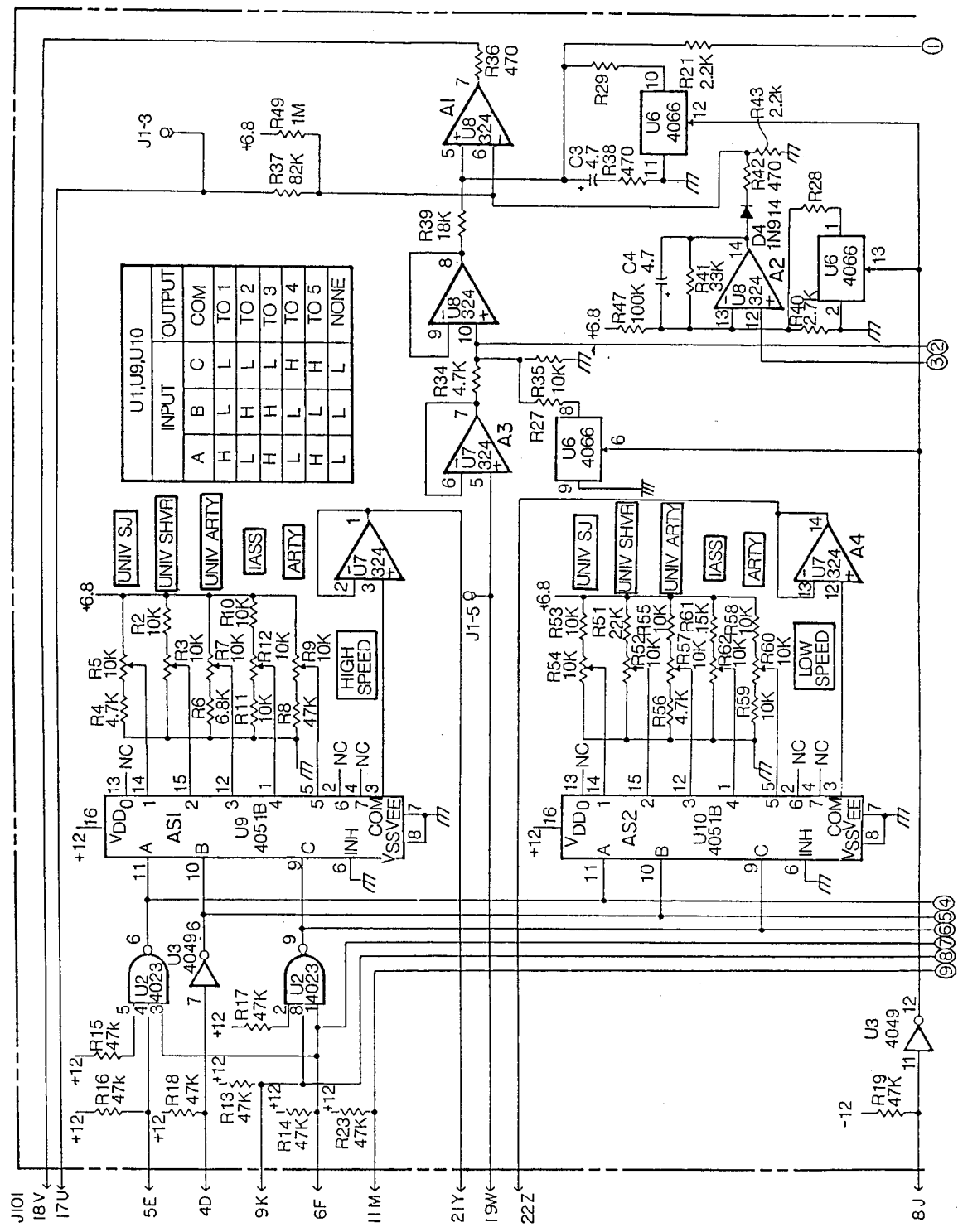

The following is a brief description of the system circuitry, shown in FIGS. 7 through 7d.

1. Functional mode selection. The selection is made by three position rotary switch 68 at the lower right of the front panel. When this switch is in the CHARGE position, current from the charger can enter the power unit through resistor R1, which produces a small voltage drop. This voltage operates LED charging indicator D1. In the ON position, LED D2 on the front panel lights, and power is supplied to the selected output. In the OFF position, all circuits are inactive and no power is drained from the batteries.

2. Charge remaining and charging rate indicators. During rapid charging, charging rate LED D1 on the front panel glows steadily. When the battery is fully charged, D1 lights sporadically or not at all because there is little current through resistor R1. In either the CHARGE or ON mode, bargraph B1 indicates the charge remaining in the batteries. Trim pots P1 and P2 set the baseline and set values. Transistor T1 provides a reference voltage.

3. Motor Drive Selection. Triple pole rotary selector switch S1 on the front panel allows power to be delivered to the handpiece power outputs. This switch also controls a logic (ground) signal on one of three lines to tell the rest of the circuit which motor drive unit has been selected.

4. Surgical Device Sensing and Logic Control. Two magnetic reed switches (34, 34') in the handpiece 10 are controlled by the attached device. Their configuration provides two logical bits to cover the four possibilities: no device, Shaver/Cutter device 12, Arthroplasty/Synovial Resector device 14, or Small Joint device 16.

Assembly of device 12 with the handpiece causes magnetic 36 to actuate opposed reed switch 34, switch 34' is not activated. Similarly, assembly of device 14, having magnets 36, 36', with the handpiece actuates both switches. Assembly of device 16 with the handpiece causes only switch 36' to actuate. (If no device is in position, neither switch is actuated.) Thus the system is able to identify the device which has been assembled with the handpiece.

This information and the position of motor drive selector switch 58 are input to several decoding circuit selectors. In each case, current appears on only one output line (or none if handpiece is attached). The circuitry on that output line is used to control power delivered to the motor drive. This scheme allows independent adjustment of the voltage/current profile for each combination of motor drive and device. In addition, another decoding circuit selector delivers voltage to one of the LEDs (D3, D4, or D5) on the front panel to show which device has been attached.

5. Speed Control. For a given handpiece, device and torque demand, speed is nearly proportional to supplied voltage. Current varies little if the voltage is increased to speed up the rotation at constant torque, because the increase in speed causes an increase in the back emf of the motor. The driving voltage is supplied through power transistor T2, whose base bias is controlled by op amp A1. A portion of the driving voltage is fed back to the reference input of A1. Motor drive speed is controlled by adjusting speed control potentiometer P3 on the front panel to vary the signal input to A1. Current sensing feedback resistor R2 develops a voltage proportional to the current through the motor. If increased resistance to rotation of the blade causes the motor to slow down, the back emf is reduced, more current flows, and the voltage across R2 increases. This voltage increases the signal input to A1, and additional voltage is supplied to the motor to restore its speed to the original value. An increase in speed caused by decreased resistance to rotation has the opposite effect. The circuit thus tends to keep the rotational speed constant as long as safe torque limits (and maximum available battery voltage) are not exceeded.

6. Speed range setting. The available range is determined by the voltages at the fixed terminals of potentiometer P3, while the wiper directs the control voltage to the regulator through op amps A3 and A4, which are used for impedance matching. The voltage at the high end of P3 is set by one of five voltage divider networks attached to decoding circuit selector AS1. The inputs to AS1 are the logic signals set by rotary selector switch S2 and by the reed switches in the motor drive unit, which indicate which device is attached. Based on these inputs, AS2 selects the voltage divider network that has been preset for the motor drive and device in use. Trim pots allow each network to be adjusted appropriately. The voltage at the low end of P3 is similarly set by voltage divider networks associated with AS2. This arrangement allows the speed range to be independently set for each handpiece/device combination.

7. Torque limit setting. For a given handpiece and device, current is nearly proportional to the torque produced. The controller/power unit limits the current so that applied torque will not excede a safe value for the device in use. Current is sensed by observing the voltage drop across resistor R2. Decoding circuit selector AS3 allows this potential to be scaled by an individually adjusted voltage divider network for each handpiece/device configuration. (This allows the torque limit to be tailored to the configuration in use, as in the case of the speed range setting described above.) The resulting voltage is the signal input to torque limiting op amp A2. When this input reaches the fixed reference level, A2 operates at very high gain to place a large signal on the reference input of A1, preventing further increase in its output. The circuit thus prevents an increase in driving voltage after the limiting current and torque have been reached.

8. Device indicators. Decoding circuit selector AS4 allows front panel indication of which device is in use. Its function is similar to that of AS1, except that AS4 has only two inputs and therefore depends only on the device. If a different handpiece is selected, AS4 is inhibited. If the handpiece 10 is selected, the outputs from AS4 allow one of the LEDs D3-D5 (70, FIG. 1) on the panel to light to signal which device is attached. If no device is attached, no LED lights and no power is delivered to the handpiece.

9. Forward/reverse. When forward rotation of the motor is selected at the footswitch, relay X1 is activated, and power is supplied in the forward direction to the motor drive selected by switch S1. When reverse is selected at the footswitch, relay X2 is activated and current to the motor drive flows in the opposite direction.

OTHER EMBODIMENTS

Other embodiments of the invention are within the following claims. For example, the surgical device and rotary tip may be provided as an integral unit. Where desired, the indicators may identify operational limits in addition to or those other than power. Also, the controller/power unit may be integral with the handpiece.

What is claimed is:

1. A surgical system adapted to operate a set of different surgical devices having different operational limits, comprising:

a handpiece adapted to alternately receive a proximal portion of each of said surgical devices, said set of said surgical devices,
  each of said surgical devices having an indicator on its proximal portion that denotes its operational limit,
  said handpiece including automatic sensor means for sensing said indicator;
  a motor for driving said handpiece; and
  means responsive to said sensor to automatically establish the operational limit of said motor in accordance with the respective surgical device received by said handpiece.

2. The surgical system of claim 1 wherein said sensor comprises means for limiting the torque applied by the motor.

3. The surgical system of claim 1 wherein said sensor comprises means for limiting the range of speed of the motor.

4. The surgical system of claim 1 wherein said motor is electrical and has an associated power source, and said sensor means is responsive to said indicator of a given surgical device to establish a limit on the electrical power delivered by said power source.

5. The surgical system of claim 4 in which said sensor means is responsive to limit the voltage applied to said motor and said motor is adapted to maintain its speed in accordance with the voltage applied.

6. The surgical system of claim 4 in which said sensor means is responsive to limit the electrical current applied to said motor to limit the torque delivered by said motor.

7. The surgical system of claim 1 wherein said indicator for each of said set of surgical devices comprises a magnet means adapted to produce a magnetic field different from that of other surgical devices of said set, said sensor means in said handpiece being responsive to said magnetic field to switch said motor to the respective operational limit.

8. The surgical system of claim 1 wherein said surgical devices include magnets in their proximal portions and said automatic sensor means of said handpiece comprises a set of switches actuatable by the presence of said magnets to establish the operational limit of said motor.

9. The surgical system of claim 1 wherein at least one surgical device of said set comprises, at its distal portion, removable rotary tips that have the operational limits of rotation indicated to said sensor means by that said surgical device.
  each said surgical device of said set having a vacuum passage connectible at one end to a vacuum passage of a respective rotary tip and, adjacent the other end, to a vacuum passage associated with said handpiece and connected proximally to a source of vacuum,
  whereby tissue severed by said rotary tip can be removed from the surgical site.

10. An arthroscopic handpiece for use in a surgical system comprising said handpiece, a set of surgical devices having different operational limits, each surgical device having on its proximal portion an indicator means for denoting its operational limit, and a motor for driving said handpiece;
  said handpiece comprising automatic sensor means adapted for sensing one of said indicator means denoting the operational limit of a respective surgical device received by said handpiece, said arthroscopic handpiece having means adapted to alternatively receive a proximal portion of said surgical device of the set for operation of the surgical device at its indicated operational limit, and said handpiece also comprising rotation means for rotating a member within the handpiece wherein said member has means adapted to be associated with a respective surgical device, said rotation means adapted to be driven by said motor, said handpiece further comprising means responsive to said automatic sensor means for controlling said rotation means, thereby establishing the operational limit, and
  said handpiece adapted for operation of a surgical device comprising, at its distal portion, a rotary tip that has an operational limit of rotation indicated by that surgical device,
  each surgical device defining a vacuum passage connectible at one end to a vacuum passage of a respective rotary tip, said arthroscopic handpiece defining a vacuum passage having means adapted for connection to the vacuum passage of the surgical device and for connection proximally to a source of vacuum for removal of tissue severed by operation of the rotary tip from the surgical site through the vacuum passage of said handpiece.

* * * * *